US009738861B2

(12) United States Patent
Nakatsuji et al.

(10) Patent No.: US 9,738,861 B2
(45) Date of Patent: Aug. 22, 2017

(54) CULTURE SYSTEM FOR PLURIPOTENT STEM CELLS AND METHOD FOR SUBCULTURING PLURIPOTENT STEM CELLS

(71) Applicants: KYOTO UNIVERSITY, Kyoto (JP); Nipro Corporation, Osaka (JP)

(72) Inventors: Norio Nakatsuji, Kyoto (JP); Yoshihiro Yoshikawa, Osaka (JP); Masakatsu Takeuchi, Osaka (JP); Daiki Tateyama, Osaka (JP)

(73) Assignees: KYOTO UNIVERSITY, Kyoto (JP); Nipro Corporation, Osaka (JP)

( * ) Notice: Subject to any disclaimer, the term of this patent is extended or adjusted under 35 U.S.C. 154(b) by 164 days.

(21) Appl. No.: 14/771,358

(22) PCT Filed: Feb. 20, 2014

(86) PCT No.: PCT/JP2014/054066
§ 371 (c)(1),
(2) Date: Nov. 5, 2015

(87) PCT Pub. No.: WO2014/136581
PCT Pub. Date: Sep. 12, 2014

(65) Prior Publication Data
US 2016/0060588 A1    Mar. 3, 2016

(30) Foreign Application Priority Data

Mar. 6, 2013    (JP) ................................ 2013-044727

(51) Int. Cl.
*C12M 1/00*    (2006.01)
*C12M 1/34*    (2006.01)
*C12M 1/12*    (2006.01)

(52) U.S. Cl.
CPC ............ *C12M 23/58* (2013.01); *C12M 23/14* (2013.01); *C12M 25/02* (2013.01); *C12M 29/00* (2013.01); *C12M 29/04* (2013.01); *C12M 41/00* (2013.01)

(58) Field of Classification Search
CPC ...... C12M 23/14; C12M 29/00; C12M 41/00; C12M 23/58; C12M 25/02; C12M 29/04
See application file for complete search history.

(56) References Cited

U.S. PATENT DOCUMENTS

2009/0311781 A1    12/2009    Amit et al.
2010/0093053 A1    4/2010    Oh et al.
(Continued)

FOREIGN PATENT DOCUMENTS

EP    1903101 A1    3/2008
JP    64-005486    1/1989
(Continued)

*Primary Examiner* — Gautam Prakash
(74) *Attorney, Agent, or Firm* — Marshall, Gerstein & Borun LLP

(57) ABSTRACT

A culture system has a culture bag for suspending and culturing pluripotent stem cells in a culture medium; a waste liquid container for storing used culture medium that is connected to the culture bag; a fresh medium container for storing a fresh culture medium that is connected to the culture bag; three-way stopcocks for switching flow channels from the culture bag to the waste liquid container or the fresh culture medium container, etc.; a trap portion for trapping the pluripotent stem cells in the culture medium in the flow toward the waste liquid container side; and a filter portion for subculturing that is formed in fourth and fifth flow channels in parallel to a first flow channel. The first flow channel connects the trap part to the culture bag, and has a mesh by which a cell mass of the pluripotent stem cells can be divided. A pump is used to pump the liquid in the individual flow channels.

9 Claims, 6 Drawing Sheets

(56) References Cited

U.S. PATENT DOCUMENTS

| | | |
|---|---|---|
| 2010/0136690 A1 | 6/2010 | Sundstrom et al. |
| 2010/0144033 A1 | 6/2010 | Mandalam et al. |
| 2011/0014693 A1 | 1/2011 | Oh et al. |
| 2011/0294210 A1 | 12/2011 | Oh et al. |
| 2012/0122209 A1 | 5/2012 | Reubinoff et al. |
| 2012/0225480 A1 | 9/2012 | Amit et al. |
| 2014/0193903 A1 | 7/2014 | Oh et al. |

FOREIGN PATENT DOCUMENTS

| | | |
|---|---|---|
| JP | 2005198626 A | 7/2005 |
| JP | 2008079554 A | 4/2008 |
| JP | 2010-526530 A | 8/2010 |
| WO | WO-2007/002086 A2 | 1/2007 |
| WO | WO-2008/015682 A2 | 2/2008 |
| WO | WO-2008/120218 A2 | 10/2008 |
| WO | WO-2009/116951 A2 | 9/2009 |
| WO | WO-2011/058558 A2 | 5/2011 |

CULTURE SYSTEM FOR PLURIPOTENT STEM CELLS AND METHOD FOR SUBCULTURING PLURIPOTENT STEM CELLS

FIELD OF THE INVENTION

The present invention relates to a system for culturing pluripotent stem cells and a method for subculturing the pluripotent stem cells.

BACKGROUND

The pluripotent stem cells capable of infinitely proliferating without causing cancerization and the like and having pluripotency have been expected to be applied to cell transplantation treatment, drug discovery screening, and the like.

Heretofore, a human pluripotent stem cell line has been proliferated and maintained by plate culture of causing the human pluripotent stem cell line to adhere to feeder cells, various polymers, or the like. However, a technique of stably culturing a large amount of high quality human pluripotent stem cells has not been established yet. In particular, a former method including causing the cell line to adhere to a culture container, and then proliferating the same by subculturing has been insufficient for preparing a large amount of pluripotent stem cells which are necessary for practical use. For example, the optimal adhesion substrate material for human pluripotent stem cells in terms of quality and cost has not been developed. Moreover, complicated many stages have been necessary for the subculturing, and thus disadvantageous steps in terms of safety and cost, such as enzyme treatment, have been included.

Recently, a suspension culture method which does not require an adhesion substrate has been reported (Patent Literatures 1 to 5). According to the suspension culture method, three-dimensional culture can be performed, and therefore a large amount of pluripotent stem cells can be cultured in a smaller space.

As a method for substituting the enzyme treatment in subculturing, a method including causing a cell mass of pluripotent stem cells to pass through a micro grid for dividing the cell mass has been devised (Patent Literature 6).

CITATION LIST

Patent Literatures

Patent Literature 1: International publication No. WO 2011/058558
Patent Literature 2: International publication No. WO 2009/116951
Patent Literature 3: International publication No. WO 2008/120218
Patent Literature 4: International publication No. WO 2008/015682
Patent Literature 5: International publication No. WO 2007/002086
Patent Literature 6: Japanese Unexamined Patent Application Publication (Translation of PCT Application) No. 2010-526530

SUMMARY OF INVENTION

Technical Problem

However, a system capable of automating the culture of a large amount of pluripotent stem cells which are necessary for practical use has not been developed yet. Moreover, when the method including causing a cell mass of pluripotent stem cells to pass through a micro grid for dividing has been adopted for culturing a large amount of pluripotent stem cells, a problem that the micro grid has been clogged, so that appropriate and efficient subculturing has not been realized has occurred.

The present invention has been made in view of the problems described above. It is an object of the present invention to provide a system suitable for culturing a large amount of pluripotent stem cells.

It is another object of the present invention to provide a method suitable for subculturing a large amount of pluripotent stem cells.

Solution to Problem (1) A culture system for pluripotent stem cells according to the present invention has a culture container for suspending and culturing pluripotent stem cells in a culture medium, a waste liquid container which is connected to the culture container by flow channels through which liquid can flow and which stores a used culture medium flowing out of the culture container, a fresh culture medium container which is connected to the culture container by flow channels through which liquid can flow and which stores a fresh culture medium to be supplied to the culture container, first switching portions which switch the flow channels from the culture container to the waste liquid container or the fresh culture medium container, a trap portion which is provided in the flow channel on the side of the culture container with respect to the first switching portions and which traps the pluripotent stem cells in the culture medium in the flow to the side of the waste liquid container, a subculturing filter portion which is provided in flow channels provided in parallel to a flow channel connecting the trap portion and the culture container between the trap portion and the culture container and which has a mesh capable of dividing a cell mass of the pluripotent stem cells, and second switching portions which switch flow channels from the trap portion to the culture container or the subculturing filter portion.

When exchanging culture media in culturing pluripotent stem cells, a culture medium is made to flow out of the culture container into the waste liquid container. Although the pluripotent stem cells flow out of the culture container together with the culture medium, the pluripotent stem cells are trapped by the trap portion, and therefore the pluripotent stem cells do not flow into the waste liquid container. After the first switching portion is switched, a fresh culture medium flows out of the fresh culture medium container into the culture container. Due to the fact that the fresh culture medium passes through the trap portion toward the culture container, the pluripotent stem cells trapped by the trap portion flow into the culture container together with the fresh culture medium. In this operation, the second switching portion is switched to the flow channel to the culture container not via the subculturing filter portion from the trap portion. Thus, the culture medium of the culture container is exchanged, and then the pluripotent stem cells are cultured in the fresh culture medium.

In subculturing, a culture medium is made to flow out of the culture container into the waste liquid container, and then the pluripotent stem cells are trapped by the trap portion similarly as described above. Before a fresh culture medium is made to flow out of the fresh culture medium container into the culture container, the second switching portion is switched to the flow channel to the culture container through the subculturing filter portion from the trap portion. The cell mass of the pluripotent stem cells which reaches the subculturing filter portion from the trap portion together with the fresh culture medium is divided when passing through the mesh. The cell masses of the pluripotent stem cells which are divided into a size suitable for subculturing flows into the culture container together with the fresh culture medium. Thus, the pluripotent stem cells are subcultured.

(2) The culture system for pluripotent stem cells according to the present invention may further have a backwashing container which is provided in a flow channel connecting the culture container and the subculturing filter portion in such a manner as to allow passage of liquid and which stores a backwashing culture medium to be supplied to the subculturing filter portion.

In subculturing, the cell mass of the pluripotent stem cells which reaches the subculturing filter portion from the trap portion together with the fresh culture medium is divided when passing through the mesh but there is a cell mass which clogs the mesh without being divided. Due to the fact that the backwashing culture medium is made to flow into the mesh from the backwashing container, the clogging cell masses are made to flow to the backwashing culture medium to be separated from the mesh. Thus, the clogging of the mesh can be eliminated.

(3) The culture system for pluripotent stem cells according to the present invention may further have a control portion for controlling the flow rate of liquid in each of the flow channels, in which the control portion may set the flow rate per unit square cm of liquid passing through the mesh of the subculturing filter portion to 95 mL or more per minute.

In subculturing, by setting the flow rate per unit square cm of the mesh of the subculturing filter portion to 95 mL or more per minute, the recovery rate of the pluripotent stem cells improves.

(4) The culture system for pluripotent stem cells according to the present invention may further have a pump for letting liquid flow through each of the flow channels, and a control portion which controls the drive of the pump, in which the control portion may drive the pump at a fixed flow rate of 90 mL or more per minute at least in the flow from the trap portion to the subculturing filter portion.

In subculturing, by letting the culture medium flow into the subculturing filter portion at a fixed flow rate of 90 mL or more per minute, the recovery rate of the pluripotent stem cells improves.

(5) As the pluripotent stem cells, ES cells or iPS cells are mentioned.

(6) As the pluripotent stem cells, human-derived pluripotent stem cells are mentioned.

(7) A method for subculturing pluripotent stem cells according to the present invention includes a culturing process of suspending and culturing a cell mass of pluripotent stem cells, a first dividing process of letting the cell mass of the cultured pluripotent stem cells flow into a mesh, which is provided in a flow channel through which a culture medium can flow, in one direction together with a culture medium to thereby divide the cell mass, and then accommodating the divided cell masses in a culture container, a backwashing process of closing a flow channel to the culture container, and then letting the culture medium flow into the mesh in an opposite direction to the direction in the dividing process to remove a cell mass clogging the mesh, and a second dividing process of opening the flow channel to the culture container, letting the removed cell mass flow in one direction together with the culture medium to thereby divide the cell mass, and then accommodating the divided cell masses in the culture container.

Thus, the cell mass clogging the mesh in the first dividing process is separated from the mesh in the backwashing process to eliminate the clogging, and the cell mass separated from the mesh in the second dividing process can be divided, and therefore the recovery rate of the pluripotent stem cells in the subculturing improves.

(8) As the pluripotent stem cells, ES cells or iPS cells are mentioned.

(9) As the pluripotent stem cells, human-derived pluripotent stem cells are mentioned.

Advantageous Effects of Invention

According to the culture system for pluripotent stem cells according to the present invention, a large amount of pluripotent stem cells can be cultured and an automated system can be realized.

Moreover, according to the method for subculturing pluripotent stem cells of the present invention, clogging of a mesh is suppressed and subculturing of a large amount of pluripotent stem cells can be realized.

EMBODIMENT FOR CARRYING OUT THE INVENTION

Hereinafter, an embodiment of the present invention is described with reference to the drawings. This embodiment is merely an example of the present invention, and it is a matter of course that this embodiment may be altered as appropriate in the range where the scope of the present invention is not altered.

[Culture System 10]

Figure 1:
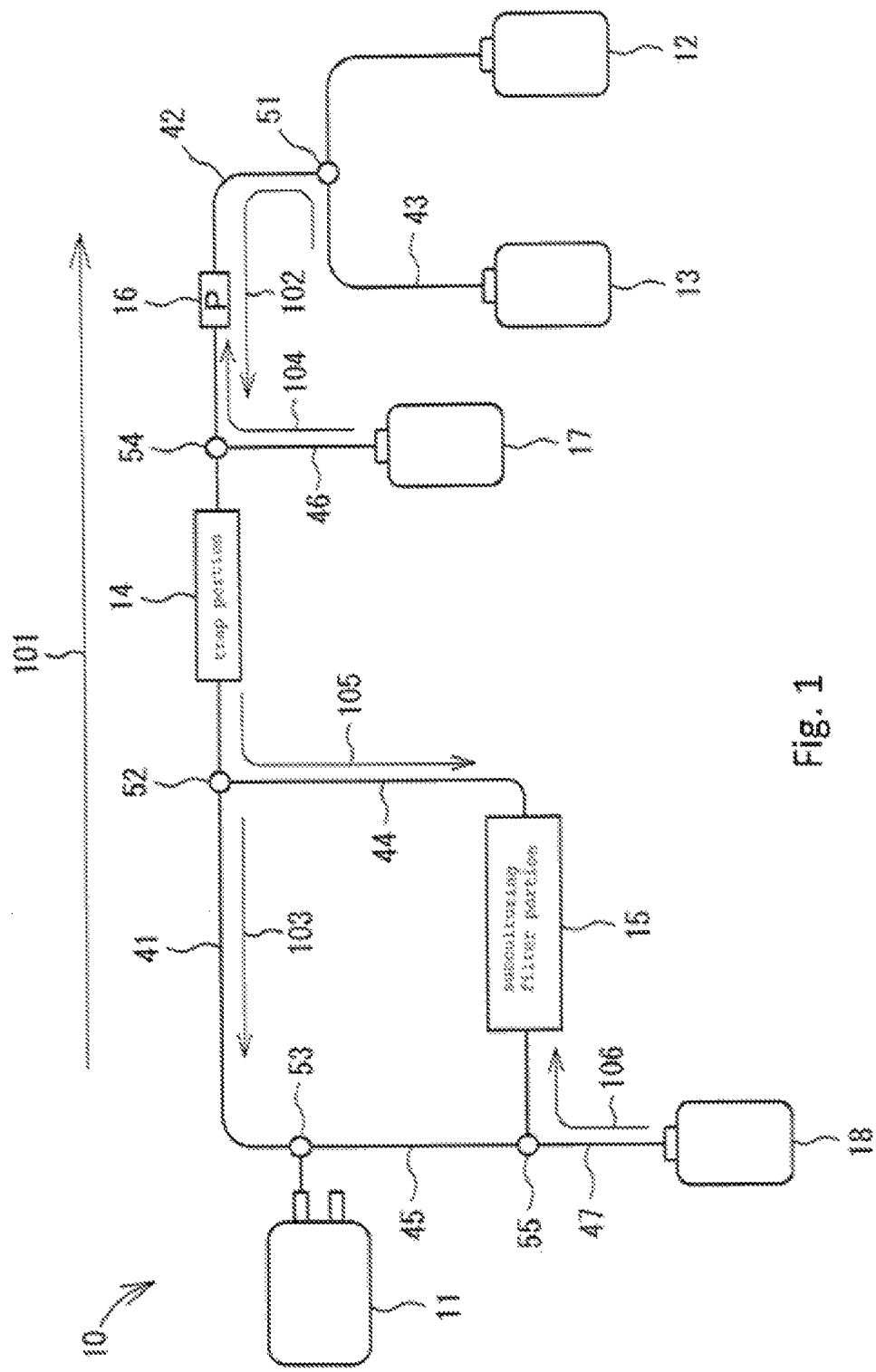
FIG. 1 is a schematic view illustrating the outline of a culture system 10 according to an embodiment of the present invention.

As illustrated in FIG. 1, in a culture system 10 for pluripotent stem cells, a culture bag 11, a waste liquid container 12, a fresh culture medium container 13, a trap portion 14, a subculturing filter portion 15, a pump 16, and backwashing containers 17 and 18 are connected by flow channels.

The culture bag 11 is a bag formed with resin capable of suspending and culturing pluripotent stem cells in a culture medium and capable of sealing liquid in the internal space. A resin sheet configuring the outer wall of the culture bag 11 is preferably one having high permeability of gas, such as carbon dioxide. The culture bag 11 is provided with a port, which allows a fluid, such as a culture medium, to flow into/out of the internal space, as appropriate. The culture bag 11 has a rectangular outer shape as viewed in plane but the shape is not particularly limited. The shape and the capacity are set in consideration of the capacity of a culture medium to be charged, operability, and the like.

Although not illustrated in FIG. 1, the culture bag 11 is accommodated in an incubator or the like in such a manner that the environment around the culture bag 11 has a temperature and humidity suitable for culturing. In order to prevent aggregation of cell masses of pluripotent stem cells, a mechanism of changing the attitude of the culture bag 11 may be provided as necessary.

The waste liquid container 12 is a container capable of storing a used culture medium and the like which are made to flow out of the culture bag 11 for exchanging culture media. The shape and the capacity of the waste liquid container 12 are set as appropriate according to the capacity of the culture bag 11, the days while the used culture medium is to be stored, and the like.

The fresh culture medium container 13 is a container capable of storing a fresh culture medium to be supplied to the culture bag 11 in exchanging culture media. The shape and the capacity of the fresh culture medium container 13 are set as appropriate according to the capacity of the culture bag 11, the frequencies of exchanging culture media, and the like.

Figure 2:
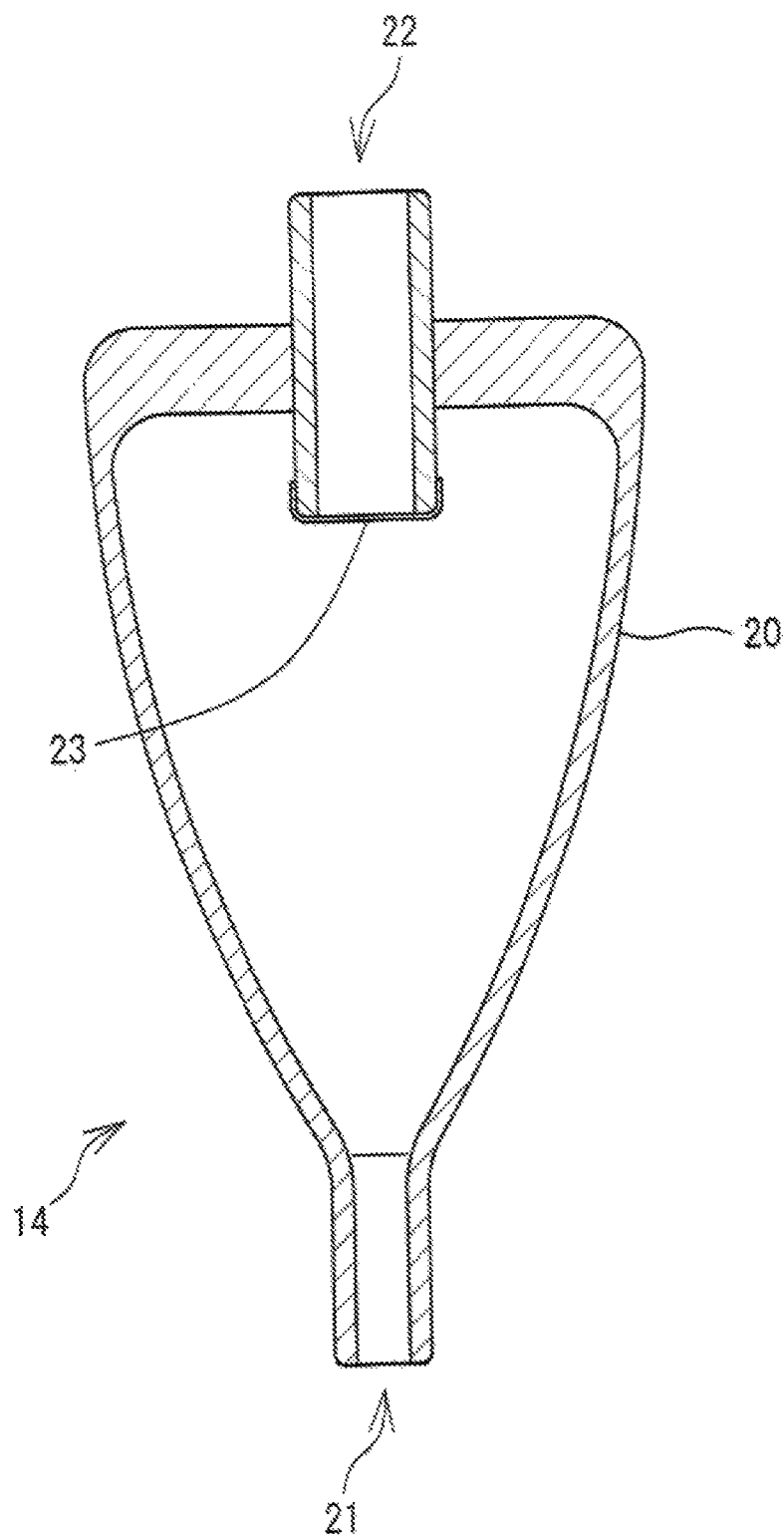
FIG. 2 is a cross sectional view illustrating the internal structure of a trap portion 14.

As illustrated in FIG. 2, the trap portion 14 traps the cell mass of the pluripotent stem cells flowing into the trap portion 14 together with the culture medium, and then lets only the culture medium flow out of the trap portion 14. In the trap portion 14, an inflow port 21 is formed in the lower side of an almost tubular-shaped body 20 and an outlet port 22 is formed in the upper side of the body 20. The inflow port 21 leads to the internal space of the body 20. The cell mass of pluripotent stem cells can flow into the internal space of the body 20 together with the culture medium through the inflow port 21.

The outlet port 22 leads to the internal space of the body 20, and a mesh 23 is provided in the outlet to the internal space of the body 20. The mesh 23 has a thin film shape in which a large number of pores having a size which does not allow passage of the cell mass of the pluripotent stem cells are formed. The cell mass of the pluripotent stem cells flowing into the internal space of the body 20 together with the culture medium from the inflow port 21 stays in the lower side of the internal space of the body 20 by own weight. The cell mass of the pluripotent stem cells which reaches the upper side in the internal space of the body 20 is obstructed by the mesh 23, and does not flow out of the outlet port 22.

Although not illustrated in each figure, in order to prevent aggregation of the cell masses of the pluripotent stem cells and clogging of the mesh 23, the trap portion 14 may be provided with a mechanism of elastically deforming the body 20 or applying vibration to the mesh 23 as necessary.

Figure 3:
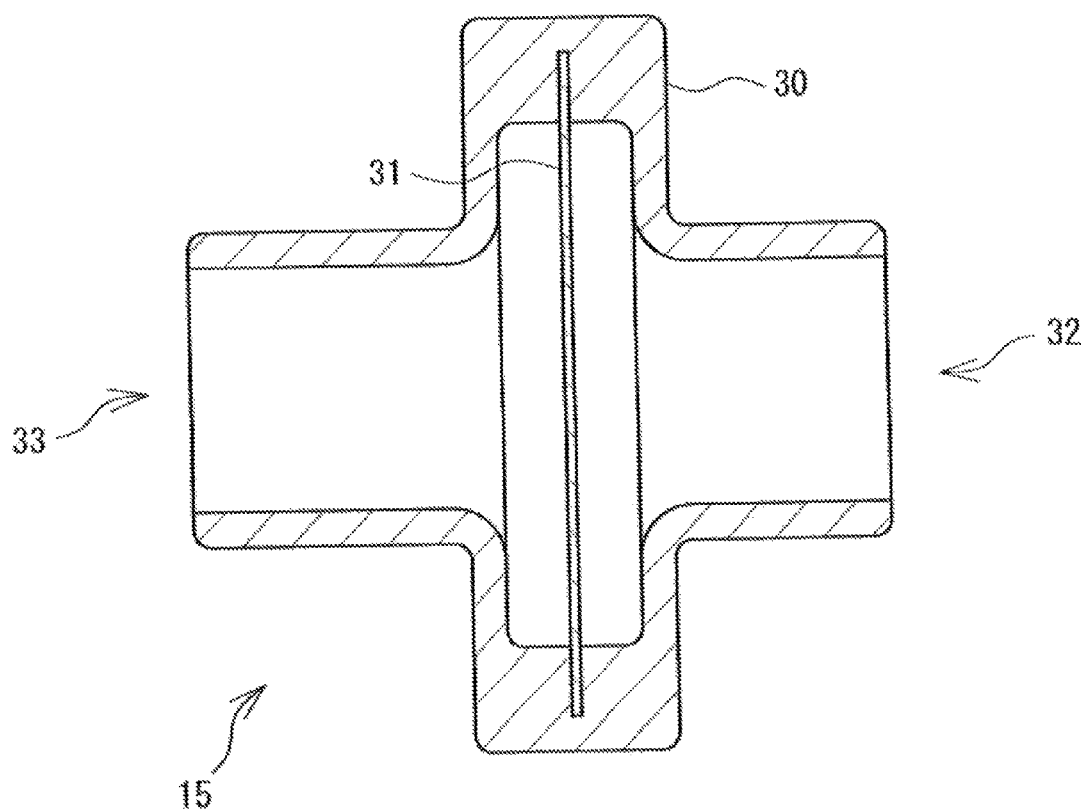
FIG. 3 is a cross sectional view illustrating the internal structure of a subculturing filter portion 15.

As illustrated in FIG. 3, the subculturing filter portion 15 divides the cell mass of the pluripotent stem cells flowing into the subculturing filter portion 15 together with the culture medium. The subculturing filter portion 15 has a body 30 accommodating a mesh 31. The body 30 has an inflow port 32 and an outlet port 33. The inflow port 32 and the outlet port 33 lead to the internal space of the body 30. The mesh 31 is provided in the internal space of the body 30 in such a manner as to separate a flow channel leading to the outlet port 33 from the inflow port 32.

Materials of the mesh 31 are not particularly limited insofar as the materials can be sterilized, and, for example, synthetic resin, such as nylon and polyethylene terephthalate, and metals, such as stainless steel, may be selected. The mesh 31 formed with stainless steel is preferable because the thickness of fibers configuring the mesh 31 can be reduced and the opening ratio (proportion of openings (pores) per unit area of the mesh 31) can be increased. When the opening ratio of the mesh 31 is larger, the recovery rate of the pluripotent stem cells to be collected by the culture bag 11 tends to be better.

The pore size of the mesh 31 may be set in such a manner that the average diameter of the cell masses after division is about 80 to 120 µm and preferably about 80 µm. For example, in the case of a stainless steel mesh, the pore size is about 40 to 100 µm, preferably 50 to 70 µm, and more preferably about 50 µm. The term "about" used herein means that ±10% is permitted. The shape and the like of the mesh 31 are not particularly limited. It is preferable for the mesh 31 to have a thickness and a shape which do not damage cells as much as possible. When the area of a region through which the cell mass can pass in the mesh 31 is larger, the number of the cell masses increases but clogging is hard to occur, and thus it is preferable.

The pump 16 lets a culture medium and the like flow in each flow channel and a peristaltic pump is mentioned as a typical example. Although not illustrated in each figure, the pump 16 has an arithmetic unit as a control portion, which operates in such a manner that the pump 16 lets a culture medium and the like flow at a flow rate according to the input flow rate.

In this embodiment, the pump 16 is used as a drive source of letting a culture medium and the like flow in each flow channel. However, in place of the pump 16, for example, a culture medium may be made to flow out of the culture bag 11 or a culture medium may be made to flow into the waste liquid container 12 and the like by compressing and deforming the culture bag 11 and the like or fluctuating the pressure of the air layer of the waste liquid container 12 and the like. Moreover, by changing the relative height relationship between the culture bag 11, and the waste liquid container 12 and the fresh culture medium container 13 by utilizing the gravity, a culture medium and the like may be made to flow between the culture bag 11, and the waste liquid container 12 and the fresh culture medium container 13, for example.

Hereinafter, flow channels connecting each of the culture bag 11, the waste liquid container 12, the fresh culture medium container 13, the trap portion 14, the subculturing filter portion 15, the pump 16, and the backwashing containers 17 and 18 are described. Each flow channel is configured from a resin tube, for example, and the internal diameter, the length, and the like are selected as appropriate according to the flow amount, the flow rate, and the like. The tubes configuring the flow channels may be configured from one tube or may be configured by connecting a plurality of tubes with a joint or the like.

The culture bag 11 is connected to the trap portion 14 by a first flow channel 41. The first flow channel 41 connects a port of the culture bag 11 and the inflow port 21 of the trap portion 14. The trap portion 14 is connected to the waste liquid container 12 by a second flow channel 42. The second flow channel 42 connects the outlet port 22 of the trap portion 14 and the waste liquid container 12. The pump 16 is provided in the second flow channel 42. The pump 16 sends liquid in one direction in the second flow channel 42 by selectively pulsating the tube configuring a part of the second flow channel 42 to the trap portion 14 side or the waste liquid container 12 side.

A three-way stopcock 51 is provided between the waste liquid container 12 and the pump 16 in the second flow channel 42. The three-way stopcock 51 is connected to the fresh culture medium container 13 by a third flow channel 43. By switching the three-way stopcock 51, the trap portion 14 is selectively connected to the waste liquid container 12 or the fresh culture medium container 13.

Two three-way stopcocks 52 and 53 are provided in the first flow channel 41. The three-way stopcock 52 is connected to the subculturing filter portion 15 by a fourth flow channel 44. The fourth flow channel 44 connects the three-way stopcock 52 and the inflow port 32 of the subculturing filter portion 15. By switching the three-way stopcock 52, the trap portion 14 is selectively connected to the culture bag 11 or the subculturing filter portion 15.

The three-way stopcock 53 is connected to the subculturing filter portion 15 by a fifth flow channel 45. The fifth flow channel 45 connects the three-way stopcock 53 and the outlet port 33 of the subculturing filter portion 15. By switching the three-way stopcock 53, the culture bag 11 is selectively connected to the trap portion 14 or the subculturing filter portion 15.

A three-way stopcock 54 is provided between the trap portion 14 and the pump 16 in the second flow channel 42. The three-way stopcock 54 is connected to the backwashing container 17 by a sixth flow channel 46. By switching the three-way stopcock 54, the pump 16 is selectively connected to the trap portion 14 or the backwashing container 17.

A three-way stopcock 55 is provided between the culture bag 11 and the subculturing filter portion 15 in the fifth flow channel 45. The three-way stopcock 55 is connected to the backwashing container 18 by a seventh flow channel 47. By switching the three-way stopcock 55, the subculturing filter portion 15 is selectively connected to the culture bag 11 or the backwashing container 18.

Although not illustrated in each figure, each of the three-way stopcocks 51 to 55 may be configured to be switchable by drive transmitted from a drive source, such as a motor. The switching of each flow channel may be realized by a valve and the like other than the three-way stopcocks. The three-way stopcocks 51 and 54 are equivalent to the first switching portions and the three-way stopcocks 52, 53, and 55 are equivalent to the second switching portions.

[Culturing of Pluripotent Stem Cells]

The culture system 10 can be used for culturing pluripotent stem cells. The pluripotent stem cells which can be cultured by the culture system 10 are not particularly limited insofar as the pluripotent stem cells are undifferentiated cells having "self-replication ability" which allows proliferation while maintaining the undifferentiated state and "differentiation/pluripotency" which allows differentiation into all the three germ layers. Examples of such pluripotent stem cells include, for example, in addition to ES cells and induced pluripotent stem cells (iPS cells), mutipotent germline stem (mGS) cells derived from primordial germ cells, multipotent adult progenitor cells (MAPC) isolated from the bone marrow, and the like. The ES cells may be ES cells generated from somatic cells by nuclear reprogramming. Among the above, the ES cells or the iPS cells are preferable. The culturing by the culture system 10 can be applied to arbitrary mammals in which the pluripotent stem cells are established or can be established. Examples of such mammals include, for example, human beings, mice, apes, pigs, rats, dogs, and the like and human beings or mice are preferable and human beings are particularly preferable.

The ES cells can be established by taking out an inner cell mass from the blastocyst of the fertilized ovum of a target animal, and then culturing the inner cell mass on a fibroblast feeder. The maintenance of cells by subculturing can be performed using a culture solution to which substances, such as a leukemia inhibitory factor (LIF)) and a basic fibroblast growth factor (bFGF), are added. Methods for establishing and maintaining the ES cells of human beings and apes are described in, for example, U.S. Pat. No. 5,843,780; Thomson J A, et al. (1995), Proc. Natl. Acad. Sci. USA. 92: 7844-7848; Tomson J A, et al. (1998), Science. 282: 1145-1147; H. Suemori Et Al. (2006), Biochem. Biophys. Res. Commun., 345: 926-932; M. Ueno et al. (2006), Proc. Natl. Acad. Sci. USA, 103: 9554-9559; H. Suemori et al. (2001), Dev. Dyn., 222: 273-279; H. Kawasaki et al. (2002), Proc. Natl. Acad. Sci. USA, 99: 1580-1585; Klimanskaya I, et al. (2006), Nature. 444: 481-485, and the like.

Using as the culture solution for creating the ES cells, a DMEM/F-12 culture solution (or a synthetic-medium: mTeSR, Stem Pro, and the like) supplemented with 0.1 mM 2-mercaptoethanol, 0.1 mM essential amino acids, 2 mM L-glutamic acid, 20% KSR, and 4 ng/mL bFGF, for example, and the human ES cells can be maintained at 37° C. under a wet atmosphere of 2% CO2 and 98% air (O. Fumitake et al. (2008), Nat. Biotechnol., 26: 215-224). The ES cells need to be subcultured every 3 or 4 days. In this case, the subculturing can be carried out using 0.25% trypsin and 0.1 mg/mL collagenase IV in PBS containing 1 mM CaCl2 and 20% KSR, for example.

The selection of the ES cells can be generally performed based on the expression of gene markers, such as alkaline phosphatase, Oct-3/4, and Nanog, as the index by a Real-Time PCR method. In particular, in the selection of the human ES cells, the expression of gene markers, such as Oct-3/4, Nanog, and ECAD, can be used as the index (E. Kroon et al. (2008), Nat. Biotechnol., 26: 443-452).

As a human ES cell stock, WA01 (H1) and WA09 (H9) are available from WiCell Research Institute and KhES-1, KhES-2, and KhES-3 are available from Institute for Frontier Medical Science, Kyoto University (Kyoto, Japan), for example.

Sperm stem cells are pluripotent stem cells derived from the testis and are cells serving as the origin for sperm formation. The cells can be differentiation-induced into cells of various series as in the ES cells. For example, the cells have a property which allows creation of a chimera mouse when transplanted to a mouse blastocyst (M. Kanatsu-Shinohara et al. (2003) Biol. Reprod., 69: 612-616; K. Shinohara et al. (2004), Cell, 119: 1001-1012). The cells can be self-replicated with a culture solution containing a glial cell line-derived neurotrophic factor (GDNF) and also the sperm stem cells can be obtained by repeating subculturing under the same culture condition as the culture conditions of the ES cells (Masanori Takebayashi et al. (2008), Jikken Igaku (Experimental Medicine), Volume 26, No. 5 (extra edition), pp. 41-46, and YODOSHA CO., LTD. (Tokyo, Japan)).

Embryonic germ cells are established from primordial germ cells in a fetal period and having the same pluripotency as that of the ES cells and, can be established by culturing primordial germ cells in the presence of substances, such as LIF, bFGF, and a stem cell factor (Y. Matsui et al. (1992), Cell, 70: 841-847; J. L. Resnick et al. (1992), Nature, 359: 550-551).

The induced pluripotent stem (iPS) cells are artificial stem cells derived from somatic cells which can be created by introducing a specific reprogramming factor into somatic cells in the form of DNA or protein and which have almost the same properties as those of the ES cells, e.g., differentiation/pluripotency and proliferation potency by self-replication (K. Takahashi and S. Yamanaka (2006) Cell, 126: 663-676; K. Tkahashi et al. (2007), Cell, 131: 861-872; J. Yu et al. (2007), Science, 318: 1917-1920; Nakagawa, M. et al.

Nat. Biotechnol. 26: 101-106 (2008; International publication No. WO 2007-069666). The reprogramming factor may be configured from genes which are specifically expressed in the ES cells, genes which play an important for maintaining undifferentiation gene products thereof, non-cording RNA, or the ES cells, gene products thereof, non-cording RNA, or low molecular weight compounds. Examples of genes contained in the reprogramming factors include, for example, Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall14, Esrrb, Nr5a2, Tbx3, or Glis1. These reprogramming factors may be used alone or in combination of two or more kinds thereof. Examples of combinations of the reprogramming factors include combinations described in International Publication No. WO 2007/069666, International Publication No. WO 2008/118820, International Publication No. WO 2009/007852, International Publication No. WO 2009/032194, International Publication No. WO 2009/058413, International Publication No. WO 2009/057831, International Publication No. WO 2009/075119, International Publication No. WO 2009/079007, International Publication No. WO 2009/079007, International Publication No. WO 2009/091659, International Publication No. WO 2009/101084, International Publication No. WO 2009/101407, International Publication No. WO 2009/102983, International Publication No. WO 2009/114949, International Publication No. WO 2009/117439, International Publication No. WO 2009/126250, International Publication No. WO 2009/126251, International Publication No. WO 2009/126655, International Publication No. WO 2009/157593, International Publication No. WO 2010/009015, International Publication No. WO 2010/033906, International Publication No. WO 2010/033920, International Publication No. WO 2010/042800, International Publication No. WO 2010/050626, International Publication No. WO 2010/056831, International Publication No. WO 2010/056831, International Publication No. WO 2010/068955, International Publication No. WO 2010/098419, International Publication No. WO 2010/102267, International Publication No. WO 2010/111409, International Publication No. WO 2010/111422, International Publication No. WO 2010/115050, International Publication No. WO 2010/124290, International Publication No. WO 2010/147395, International Publication No. WO 2010/147612, Huangfu D, et al. (2008), Nat. Biotechnol., 26: 795-797; Shi Y et al. (2008), Cell Stem Cell, 2: 525-528; Eminli S et al. (2008), Stem Cells. 26: 2467-2474; Huangfu D et al. (2008), Nat. Biotecnol. 26: 1269-1275; Shi Y et al. (2008), Cell Stem Cell, 3: 568-574; Zhao Y et al. (2008), Cell Stem Cell, 3: 475-479; Marson A, (2008), Cell Stem Cell, 3: 132-135; Feng B et al. (2009), Nat Cell Biol. 11: 197-203; R. L. Judson et al. (2009), Nat. Biotech., 27: 459-461; Lyssiotis C A et al. (2009): Proc. Natl. Acad Sci. USA. 106: 8912-8917; Kim J B et al. (2009), Nature. 461: 643-649; Ichida J K et al. (2009), Cell Stem Cell. 5: 491-503; Heng J C et al. (2010), Cell Stem Cell. 6: 167-174; Han J et al. (2010), Nature. 463: 1096-1100; Mali P et al. (2010), Stem Cells. 28: 713-720; Maekawa M et al. (2011), Nature. 474: 225-229.

The reprogramming factors include factors to be used for the purpose of increasing the establishment efficiency of histone deacetylase (HDAC) inhibitors (for example, low molecular weight inhibitors, such as valproic acid (VPA), tricostatin A, sodium butyrate, MC1293, and M344, nucleic acidic expression inhibitors, such as siRNA and shRNA against HDAC (for example, HDAC1 si RNA Smartpool (Registered Trademark) millipore), HuSH 29 mer shRNA Constructs against HDAC1 (OriGene and the like), and the like), MEK inhibitors (for example, PD184352, PD98059, U0126, SL327, and PD0325901), Glycogen synthase kinase-3 inhibitors (for example, Bio, CHIR99021), DNA methyl transferase inhibitors (for example, 5-azacytidine), histone methyl transferase inhibitors (for example, low molecular weight inhibitors, such as BIX-01294, nucleic acidic expression inhibitors, such as siRNA and shRNA against Suv39HL, Suv39h2, SetDB1, and G9a, and the like), L-channel calcium agonist (for example, Bayk8644), butyric acid, TGF□ inhibitors, or ALK5 inhibitors (for example, LY364947, SB431542, 616453, and A-83-01), p53 inhibitors (for example, siRNA and shRNA against p53), ARID3A inhibitors (for example, siRNA and shRNA against ARID3A), miRNA, such as miR-291-3p, miR-294, miR-295, and miR-302), Wnt Signaling (for example, soluble Wnt3a), neuropeptide Y, prostaglandins (for example, prostaglandin E2 and prostaglandin J2), hTERT, SV40LT, UTF1, IRX6, GLIS1, PITX2, DMRTB1, and the like. In this specification, the factors used for the purpose of improving the establishment efficiency thereof are not also particularly distinguished from the reprogramming factors.

In the case of the form of protein, the reprogramming factors may be introduced into somatic cells by techniques, such as lipofection, fusion with cell membrane permeable peptide (for example, TAT derived from HIV and polyarginine), and microinjection, for example.

On the other hand, in the case of the form of DNA, the reprogramming factors can be introduced into somatic cells using vectors, such as virus, plasmid, and artificial chromosome, or techniques, such as lipofection, liposome, and microinjection, for example. Examples of the virus vectors include retroviras vectors, lentivirus vectors (Cell, 126, pp. 663-676, 2006; Cell, 131, pp. 861-872, 2007; Science, 318, pp. 1917-1920, 2007), adenovirus vectors (Science, 322, 945-949, 2008), adeno-associated virus vectors, sendai virus vectors (International Publication No. WO 2010/008054), and the like. Examples of the artificial chromosome vectors include human artificial chromosome (HAC), yeast artificial chromosome (YAC), bacteria artificial chromosome (BAC, PAC), and the like, for example. As the plasmid, plasmid for mammal cells can be used (Science, 322: 949-953, 2008). The vectors can contain, in such a manner that the nuclear reprogramming substances can be expressed, control sequences of a promoter, an enhancer, a ribosome junction sequence, a terminator, a polyadenylation site, and the like and further, selective marker sequences of a drug resistant gene (for example, a kanamycin resistant gene, an ampicillin resistant gene, and a puromycin resistant gene), a thymidine kinase gene, a diphtheria toxin gene, and the like, reporter gene sequences of green fluorescent protein (GFP), βglucuronidase (GUS), and FLAG, and the like, etc., as necessary. In order to break both the genes coding the reprogramming factor or the promoter and the gene coding the reprogramming factors bonded thereto after introducing into somatic cells, the vectors may have a LoxP sequence before and after the sequences.

In the case of the form of RNA, the reprogramming factors may be introduced into somatic cells by techniques, such as lipofection and microinjection, for example, and, in order to suppress decomposition, RNA into which 5-methyl cytidine and pseudouridine (TriLink Biotechnologies) are introduced may be used (Warren L, (2010), Cell Stem Cell. 7: 618-630).

Culture solutions for iPS cell induction (These culture solutions can further contain LIF, penicillin/streptomycin, puromycin, L-glutamine, non-essential amino acids, β-mercaptoethanol, and the like as appropriate.), commercially available culture solutions (for example, a culture solution for mouse ES cell culture (TX-WES culture solution, Thrombo X), a culture solution for primate ES cell culture (primate ES/iPS cell culture solution, ReproCELL Incorporated), a serumless culture medium (mTeSR, Stemcells Technology), and the like.

As an example of a culturing method, somatic cells and the reprogramming factor are brought into contact with each other on a 10% FBS containing DMEM or a DMEM/F12 culture solution at 37° C. in the presence of 5% $CO_2$, the cells are cultured for about 4 to 7 days, the cells are seeded again on feeder cells (for example, mitomycin C treated STO cells, SNL cells, and the like), and then, about 10 days after the contact between the somatic cells and the reprogramming factor, the cells are cultured in a culture solution for culturing bFGF containing primate ES cells, so that an iPS-like colony can be produced about 30 to 45 days or longer after the contact, for example.

Or, the cells are cultured on feeder cells (for example, mitomycin C treated STO cells, SNL cells, and the like) in a 10% FBS containing DMEM culture solution (The culture solution can further contain LIF, penicillin/streptomycin, puromycin, L-glutamine, non-essential amino acids, β-mercaptoethanol, and the like as appropriate.) at 37° C. in the presence of 5% $CO_2$, so that an ES-like colony can be produced about 25 to 30 days or longer later. Preferably, a method using somatic cells themselves to be reprogrammed in place of the feeder cells (Takahashi K et al. (2009), PLoS One. 4: e8067 or International Publication No. WO 2010/137746) or a method using an extracellular matrix (for example, Laminin (International Publication No. WO 2009/123349), Matrigel (BD)) in place of the feeder cells are mentioned.

In addition thereto, a method for performing culturing using a culture medium not containing serum is also mentioned (Sun N et al. (2009), Proc Natl Acad Sci USA. 106: 15720-15725). Furthermore, in order to increase the establishment efficiency, iPS cells may be established under low oxygen conditions (oxygen concentration of 0.1% or more and 15% or less) (Yoshida Y et al. (2009), Cell Stem Cell. 5: 237-241, International Publication No. WO 2010/013845).

During the culturing, the culture solution is exchanged with a fresh culture solution once every day from the second day after starting the culturing. The number of cells of the somatic cells to be used for nuclear reprogramming is not limited and is in the range of about $5\times10^3$ to $5\times10^6$ cells per 100 $cm^2$ of a culture dish.

The iPS cells can be selected in accordance with the shape of the formed colony. On the other hand, when a drug resistant gene expressed in connection with a gene (for example, Oct3/4, Nanog) expressed when somatic cells are reprogrammed is introduced as a marker gene, the established iPS cells can be selected by performing culturing in a culture solution (selective culture solution) containing a corresponding drug. When the marker gene is a fluorescent protein gene, the established iPS cells can be selected by observation under a fluorescence microscope. In the case of a luciferase gene, the established iPS cells can be selected by adding a luminescent substrate. In the case of a chromogenic enzyme gene, the established iPS cells can be selected by adding a chromogenic substrate.

[Suspension Culture of Pluripotent Stem Cells (Culturing Process)]

The pluripotent stem cells prepared as described above are suspended and cultured by the culture system 10. Specifically, the culture bag 11 is charged with the pluripotent stem cells together with a culture medium, and then suspended and cultured until the average diameter of cell masses of the pluripotent stem cells reaches about 200 to 300 μm. The term "about" used herein means that ±10% is permitted. When the diameter of the cell mass exceeds 300 μm, there are problems that a microenvironment is formed due to cytokine and the like secreted by the cells, and differentiation is induced and further necrosis occurs in the central portion of the cell mass, so that the recovery rate of raw cells decreases. On the other hand, when the lower limit of the average diameter of the cell masses is not particularly limited insofar as the average diameter is larger than the average diameter of the cell masses when starting the suspension and culturing (when suspending in the case of suspending and culturing after subculturing). In consideration of the yield of the pluripotent stem cells, it is preferable to continue the culturing until the average diameter reaches about 200 μm or more.

As the culture medium for suspension culture, a culture medium having the same composition as that of the culture medium for adhesion culture described above can be used. Preferably, in order to prevent movement of the cell masses and adhesion of the cell masses, it is desirable to give moderate viscosity to the culture medium. Herein, the "moderate viscosity" means the viscosity at which the culture medium exchange is not hindered and the adhesion of the cell masses do not occur.

A means for giving viscosity to the culture medium is not particularly limited. The viscosity can be given to the culture medium by adding a water soluble polymer to the culture medium with a preferable concentration, for example. As the water soluble polymer, any water soluble polymer can be used insofar as moderate viscosity can be given to the culture medium and the cells are not adversely affected (no cytotoxicity) in a concentration range where viscosity can be given. Examples of the water soluble polymer include, for example, polysaccharides, such as cellulose and agarose, ethers of polysaccharides, such as methyl cellulose, ethyl cellulose, hydroxyethyl cellulose, hydroxypropyl cellulose, hydroxyethyl methyl cellulose, hydroxypropyl methylcellulose, hydroxyethyl ethyl cellulose, hydroxypropylethyl cellulose, ethyl hydroxyethyl cellulose, dihydroxypropyl cellulose, and hydroxyethyl hydroxypropyl cellulose, synthetic polymers, such as polyacrylamide, polyethylene oxide, polyvinyl pyrrolidone, an ethylene glycol/propylene glycol copolymer, polyethylene imine polyvinyl methyl ether, polyvinyl alcohol, polyacrylic acid, and a maleic acid copolymer, biopolymers, such as collagen, gelatin, hyaluronic acid, dextran, alginic acid, carrageenan, and starch, or artificial polymers (for example, elastin-like peptide and the like) imitating them. These water solubility polymers may be used alone and can also be used as a mixture of several kinds of the water soluble polymers. Moreover, copolymers of these water solubility polymers may be used. Methyl cellulose, polyethylene glycol, polyvinyl pyrrolidone, carboxymethylcellulose, or a mixture thereof is preferable and methyl cellulose is more preferable.

For example, when methyl cellulose is added to the culture medium in order to give viscosity thereto, the concentration of the methyl cellulose is preferably higher than 0.25 w/v % and lower than 0.5 w/v %. When the concentration of methyl cellulose is 0.25 w/v % or less, the viscosity is excessively low, and thus a desired effect cannot be obtained. When the concentration is 0.5 w/v % or higher, the culture medium becomes difficult to pass through the trap portion 14 and the subculturing filter portion 15. The concentration of the methyl cellulose is preferably 0.26 to 0.3 w/v % and particularly preferably 0.28 w/v %. Even when using another water soluble polymer, a person skilled in the art can select another water soluble polymer and a concentration in order to obtain the moderate viscosity described above.

In another preferable aspect, a temperature-rise type temperature sensitivity hydro-gel can be used as the water soluble polymer. The "temperature-rise type temperature sensitivity hydro-gel" refers to a hydro-gel which is liquid at a low temperature and which exhibits a reversible sol-gel phase transition in which the hydro-gel is gelated by raising the temperature and is solated again by cooling the gel to room temperature. Examples of the temperature-rise type temperature sensitivity hydro-gel include "Mebiol gel" series (Trade name, Mebiol Inc.) which exhibit a gelling transition temperature of 27 to 32° C. and the like but the temperature-rise type temperature sensitivity hydro-gel is not limited thereto. When using the temperature-rise type temperature sensitivity hydro-gel, the hydro-gel is added at a concentration at which sufficient viscosity for preventing movement of floating cell masses and adhesion of cell masses can be given, the cells are proliferated to a size suitable for subculturing by suspension culture, the culture solution is solated by cooling the same to a temperature equal to or lower than the gelling transition temperature, and then the cells are made to pass through the trap portion 14 or the subculturing filter portion 15, whereby the cells can be easily recovered.

The culturing is performed by dissociating the pluripotent stem cells subjected to the adhesion culture by enzyme treatment, seeding the cells into the culture bag 11 in such a manner that the cell density is about 0.5 to 50+104 cells/cm2 and preferably about 1 to 10+104 cells/cm2, and then culturing the cells in a $CO_2$ environment in the culture system 10 under a $CO_2$ atmosphere having a concentration of about 1 to 10% and preferably about 2 to 5% at about 30 to 40° C. preferably about 37° C. for 1 to 7 days, preferably 3 to 6 days, and more preferably 4 or 5 days.

During the culturing described above, it is preferable to exchange the culture medium in the culture bag 11 with a fresh culture medium every 1 or 2 days. When exchanging the culture medium, the culture medium is made to flow out of the culture bag 11 into the waste liquid container 12 (arrow 101). Due to the fact that the three-way stopcocks 51 to 54 are operated, the flow channel from the culture bag 11 to the waste liquid container 12 through the trap portion 14 is opened. Due to the fact that the pump 16 is operated, the culture medium flows into the waste liquid container 12 through the first flow channel 41 and the second flow channel 42 from the culture bag 11 at a fixed flow rate. The flow rate is preferably a fixed flow rate in the range of about 5 to 50 mL per minute and more preferably a fixed flow rate in the range of about 8 to 10 mL per minute.

The cell masses of the pluripotent stem cells flow out of the culture bag 11 together with the culture medium. However, since the cell masses are trapped by the trap portion 14, the cell masses do not flow into the waste liquid container 12. Specifically, the cell masses of the pluripotent stem cells flow into the internal space of the body 20 together with the culture medium from the inflow port 21 in the lower side of the body 20. In the internal space of the body 20, the cell masses stay in the lower side of the internal space of the body 20 by own weight. On the other hand, the culture medium flows out of the outlet port 22 from the internal space of the body 20. The cell masses which reach the upper side in the internal space of the body 20 are blocked by the mesh 23, and do not flow out of the outlet port 22.

When all the culture media in the culture bag 11 are made to flow out, the three-way stopcock 51 is switched, so that the culture bag 11 and the fresh culture medium container 13 are connected to each other through the trap portion 14. Due to the fact that the pump 16 is operated, a fresh culture medium flows from the fresh culture medium container 13 into the culture bag 11 through the first flow channel 41, the second flow channel 42, and the third flow channel 43 at a fixed flow rate (arrow 102). The flow rate is preferably a fixed flow rate in the range of about 50 to 150 mL per minute and more preferably a fixed flow rate in the range of about 80 to 100 mL per minute.

The fresh culture medium which flows out of the fresh culture medium container 13 flows into the internal space of the body 20 from the outlet port 22 of the trap portion 14. Then, the fresh culture medium flows out of the inflow port 21, and then flows into the culture bag 11 through the first flow channel 41 together with the cell masses of the pluripotent stem cells staying in the lower side of the internal space of the body 20 (arrow 103). Thus, the cell masses of the pluripotent stem cells trapped by the trap portion 14 flow into the culture bag 11 together with the fresh culture medium.

When the cell masses clog the mesh 23 of the trap portion 14, a backwashing culture medium may be made to flow into the trap portion 14 from the backwashing container 17 in order to remove the clogging cell masses.

The backwashing culture medium is a culture medium to be used for the suspension culture described above and is preferably a culture medium to which the water soluble polymer is not added, for example. Due to the backwashing culture medium having low viscosity passes through the mesh 23 of the trap portion 14, the cell masses clogging the mesh 23 are easily separated from the mesh 23. The flow amount and the flow rate of the backwashing culture medium are selected as appropriate according to the clogging level of the mesh 23.

Specifically, when the culture medium is made to flow out of the culture bag 11 into the waste liquid container 12 through the trap portion 14, the operation of the pump 16 is suspended, and then the three-way stopcock 54 is switched, so that the backwashing container 17 and the pump 16 are connected to each other through the sixth flow channel 46. Then, due to the fact that the pump 16 is operated again, the backwashing culture medium from the backwashing container 17 flows through the second flow channel 42 toward the fresh culture medium container 13 through the sixth flow channel 46 (arrow 104). When only a predetermined amount of the backwashing culture medium flows into the second flow channel 42, the operation of the pump 16 is suspended, and then the three-way stopcock 54 is switched, so that the culture bag 11 and the fresh culture medium container 13 are connected to each other through the trap portion 14. Then, due to the fact that the pump 16 is operated in the opposite direction (direction indicated by the arrow 102), specifically in a direction from the fresh culture medium container 13 toward the trap portion 14, the backwashing culture medium flowing into the second flow channel 42 flows into the internal space of the body 20 through the outlet port 22 of the trap portion 14. At this time, the cell masses clogging the mesh 23 of the trap portion 14 are separated due to the backwashing culture medium. Then, the direction of the pump 16 is switched, so that the culture medium is made to flow out of the culture bag 11 to the waste liquid container 12 side in the same manner as described above.

The culture medium in the culture bag 11 is exchanged with a fresh culture medium every 1 or 2 days in the suspension culture.

For example, it is supposed that the average diameter of the cell masses of the pluripotent stem cells when starting the suspension culture is about 80 μm, and the cells are proliferated until the average diameter reaches about 250 μm, it is necessary to amplify the number of cells in the cell masses by about $3^3=27$ times. For example, human ES cells are divided once in about 24 hours. Therefore, it is considered that, when the cells are cultured for 4 or 5 days, the cells are proliferated to a desired size also in terms of calculation.

[Subculturing of Pluripotent Stem Cells]

The cell masses of pluripotent stem cells having a uniform size in which the average diameter of the cell masses of the pluripotent stem cells is about 200 to 300 μm are then divided into small cell masses having an almost uniform size in which the average diameter is about 80 to 120 μm to be subcultured. The term "about" used herein means that ±20% is permitted. When the cell masses are divided in such a manner that the average diameter of the cell masses is 50 μm or less, the cells are likely to cause cell death, such as apoptosis, and thus the average diameter is not preferable. The upper limit of the average diameter after division is not particularly limited. However, when the size is larger, the amplification efficiency by the suspension culture after the following subculturing further decreases. Therefore, the average diameter is preferably about 120 μm or less and particularly preferably about 40 to 80 μm.

Due to the fact that the three-way stopcocks 51 to 54 are operated after the cells are proliferated until the average diameter of the cell masses of the pluripotent stem cells is amplified to about 200 to 300 μm in the culture bag 11, the flow channel from the culture bag 11 to the waste liquid container 12 through the trap portion 14 is opened. Due to the fact that the pump 16 is operated, the culture medium flows into the waste liquid container 12 through the first flow channel 41 and the second flow channel 42 from the culture bag 11 at a fixed flow rate (arrow 101). The flow rate is preferably a fixed flow rate in the range of about 5 to 50 mL per minute and more preferably a fixed flow rate in the range of about 8 to 10 mL per minute.

The cell masses of the pluripotent stem cells flow out of the culture bag 11 together with the culture medium. However, since the cell masses are trapped by the trap portion 14 as described above, the cell masses do not flow into the waste liquid container 12. When all the culture media in the culture bag 11 are made to flow out, the three-way stopcocks 51, 52, and 53 are switched, so that the culture bag 11 and the fresh culture medium container 13 are connected to each other through the trap portion 14 and the subculturing filter portion 15.

Due to the fact that the pump 16 is operated, a fresh culture medium flows toward the culture bag 11 through the second flow channel 42, the third flow channel 43, the fourth flow channel 44, and the fifth flow channel 45 from the fresh culture medium container 13 at a fixed flow rate (arrow 102). The fresh culture medium which flows out of the fresh culture medium container 13 flows into the internal space of the body 20 from the outlet port 22 of the trap portion 14, and then flows out of the inflow port 21 together with the cell masses of the pluripotent stem cells staying in the lower side of the internal space of the body 20 in the same manner as described above. Thus, the cell masses of the pluripotent stem cells trapped by the trap portion 14 flow into the subculturing filter portion 15 with the fresh culture medium (arrow 105).

The cell masses of the pluripotent stem cells which reach the subculturing filter portion 15 together with the fresh culture medium from the trap portion 14 are divided when passing through the mesh 31. The flow rate when letting the cell masses of the pluripotent stem cells pass through the mesh 31 is preferably a fixed flow rate in the range of about 90 to 300 mL/min. The term "about" used herein means that ±10% is permitted. The flow rate is the flow rate in the second flow channel 42 or the fourth flow channel 44 caused by the driving force of the pump 16. When the flow rate is lower than about 90 mL/min, the number of the cell masses which cannot pass through the mesh 31 increases, so that the recovery rate of the pluripotent stem cells collected by the culture bag 11 decreases. The upper limit of the flow rate is not particularly limited. However, when the flow rate is higher than about 300 mL/min, the average diameter of the cell masses passing through the mesh 31 tends to be small.

When the area (effective area) through which the cell masses of the pluripotent stem cells can pass in the mesh 31 is enlarged, the cross-sectional area of the space where the mesh 31 is present in the body 30 to the cross-sectional area of the fourth flow channel 44 becomes large, and, as a result, the flow rate of the cell masses (culture medium) which pass through the region tends to be lower as approaching the periphery of the mesh 31. Accordingly, the area of the cell mass passing through the mesh 31 may also change when the effective area of the mesh 31 changes. Therefore, the flow rate when letting the cell masses of the pluripotent stem cells pass through the mesh 31 may be grasped as a flow rate per unit square cm of the mesh 31. For example, when the effective diameter of the mesh 31 having a disk shape is 11 mm, the flow rate per unit square cm of the mesh 31 is preferably in the range of about 95 to 315 mL/min.

The process of letting the cell mass of the pluripotent stem cells pass through the mesh 31 with a fresh culture medium to divide the cell mass is equivalent to the first dividing process.

When the cell masses clog the mesh 31 of the subculturing filter portion 15, a backwashing culture medium may be made to flow into the subculturing filter portion 15 from the backwashing container 18 in order to remove the clogging cell masses. Specifically, the operation of the pump 16 is suspended, and then the three-way stopcock 55 are switched, so that the backwashing container 18 and the subculturing filter portion 15 are connected to each other through the seventh flow channel 47. Then, when the pump 16 is operated in the opposite direction (rightward in the subculturing filter portion 15 of FIG. 1), the backwashing culture medium from the backwashing container 18 back-flows through the mesh 31 toward the inflow port 32 from the outlet port 33 of the subculturing filter portion 15 (arrow 106).

The backwashing culture medium is a culture medium to be used for the suspension culture described above and is preferably one to which the water soluble polymer is not added, for example. Due to the fact that the backwashing culture medium having low viscosity passes through the mesh 31 of the subculturing filter portion 15, the cell masses clogging the mesh 31 are easily separated from the mesh 31. The flow amount and the flow rate of the backwashing culture medium are selected as appropriate according to the clogging level of the mesh 31.

After the backwashing is completed, the operation of the pump 16 is suspended, and then the three-way stopcock 55 is switched, so that the culture bag 11 and the subculturing filter portion 15 are connected to each other. Then, due to the fact that the pump 16 is operated in a forward direction (leftward in the subculturing filter portion 15 of FIG. 1) again (arrow 105), a fresh culture medium is made to flow out of the fresh culture medium container 13 into the culture bag 11 in the same manner as described above.

The process of removing the cell masses of the pluripotent stem cells once from the mesh 31 together with the backwashing culture medium, and then letting the cell masses pass through the mesh 31 again to divide the same as described above is equivalent to the second dividing process.

The cell masses of the pluripotent stem cells which are divided into a size suitable for subculturing flow into the culture bag 11 together with the fresh culture medium. Thus, the pluripotent stem cells are subcultured.

Working Effects of this Embodiment

According to the culture system 10 of pluripotent stem cells according to this embodiment, a large amount of pluripotent stem cells can be cultured and an automated system can be realized.

Moreover, even when cell masses of pluripotent stem cells which reach the subculturing filter portion 15 from the trap portion 14 together with a fresh culture medium in subculturing clog the mesh 31 without being divided, a backwashing culture medium is made to flow into the mesh 31 from the backwashing container 18, and then the clogging cell masses are carried by the backwashing culture medium to be separated from the mesh 31. Thus, the clogging of the mesh 31 of the subculturing filter portion 15 can be eliminated.

Moreover, by letting a culture medium flow into the subculturing filter portion 15 at a fixed flow rate of 90 mL or more per minute in subculturing, the recovery rate of pluripotent stem cells improves.

EXAMPLES

[Flow Rate of Culture Medium Passing through Subculturing Filter Portion 15]

The cell recovery rate when the flow rate of a culture medium passing through the subculturing filter portion 15 was set to each of 10 mL, 50 mL, 90 mL, 150 mL, and 300 mL per minute was measured. Since the effective diameter of the mesh 31 was 11 mm, the flow rate was 10.5 mL, 52.6 mL, 94.7 mL, 157.9 mL, and 315.8 mL per minute when converted to the flow rate per unit square cm of the mesh 31.
(Preparation of Reagent)

100 mL of a supplement (VERITAS Corporation, ST-05850) was added to 350 mL of a base culture medium (VERITAS Corporation, ST-05850), and then sufficiently stirred. Furthermore, 500 mL of a Y-27632 solution (SIGMA, Y0503-5MG) was added in such a manner that final concentration was 10 µm. Furthermore, 50 mL of methyl cellulose liquid (R&D, HSC001) was added, and then sufficiently stirred to prepare a subculturing culture medium.

50 mL of methyl cellulose liquid was added to 450 mL of a DMEM/F12 culture medium (Life Technologies), and then sufficiently stirred to obtain a backwashing culture medium.
(Subculture Operation)

The culture medium was made to flow out of the culture bag 11 into the trap portion 14 together with cell masses of pluripotent stem cells. The cell masses were trapped in the trap portion 14, and then only the culture medium was made to flow to the waste liquid container 12 side. In this operation, the culture medium was made to flow out of the waste liquid container 12 while letting a backwashing culture medium back-flow into the trap portion 14 from the backwashing container 17 as appropriate to eliminate clogging of the mesh 23. Then, a fresh culture medium was made to flow out of the fresh culture medium container 13 into the culture bag 11 through the trap portion 14, and then the subculturing filter portion 15. Thus, the cell masses trapped in the trap portion 14 were made to pass through the mesh 31 (formed with stainless steel, Pore size of 50 µm, Opening ratio of 64%) of the subculturing filter portion 15 to divide the cell masses to be subcultured. By letting the backwashing culture medium back-flow into the subculturing filter portion 15 from the backwashing container 18 as appropriate to eliminate the clogging of the mesh 31, and then letting the same pass through the mesh 31 again in subculturing, the clogging cell masses were also divided.
(Determination of Recovery Rate by Calculation)

The recovery rate of the pluripotent stem cells collected by the culture bag 11 after subculturing was determined by calculation. The recovery rate was determined by the following equation.

(Recovery rate)=(Total number of cells after subculturing)/(Total number of cells before subculturing)

Figure 4:
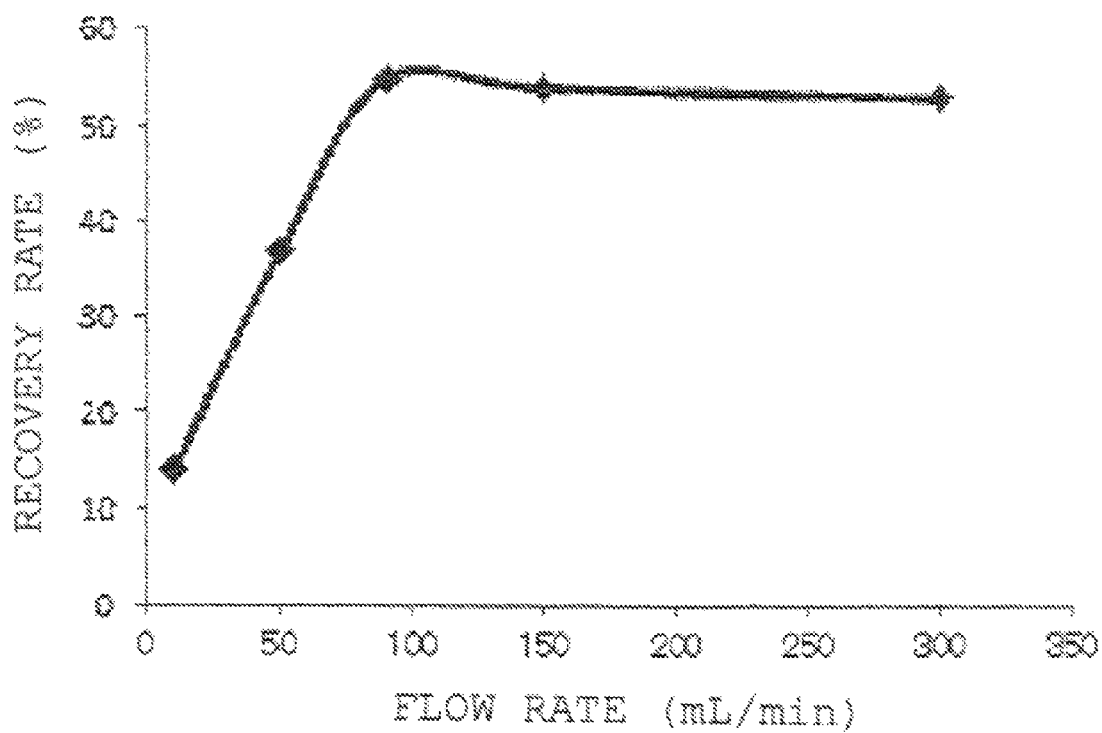
FIG. 4 shows the recovery rate of cells to the flow rate of a culture medium passing through a mesh 31.

The results are shown in FIG. 4. As is clear from FIG. 4, the tendency was confirmed that the recovery rate further improved as the flow rate when the culture medium passed through the subculturing filter portion 15 became higher and the recovery rate at flow rates of 90 mL or more per minute was fixed.
(Size of Cell Mass after Subculturing)

Figure 5:
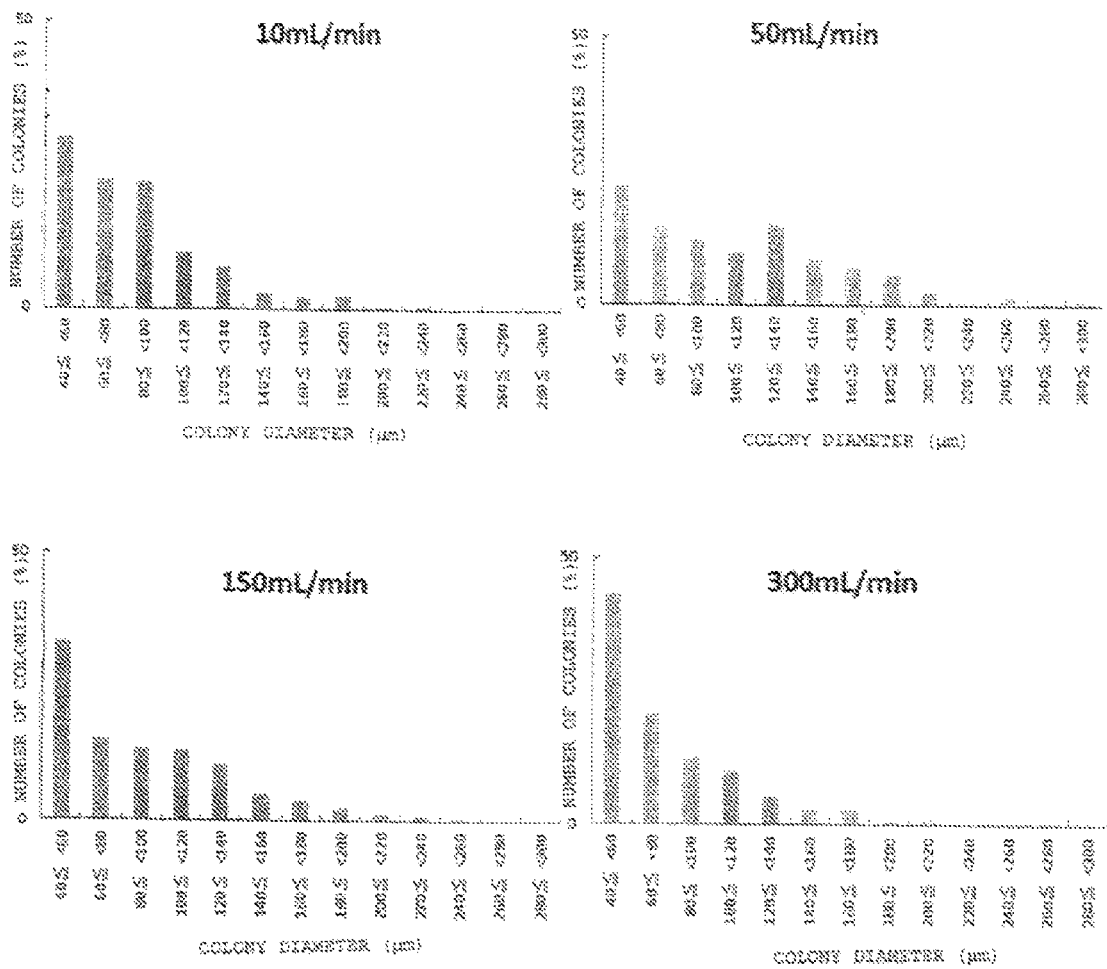
FIG. 5 show the distributions of the sizes of cell masses passing through the mesh 31.

The size and the distribution of the cell masses of the pluripotent stem cells collected by the culture bag 11 after subculturing were measured. The results are shown in FIG. 5. As is clear from FIG. 5, when the flow rate was low, the distribution of the cell masses having a size larger than the pore size of the mesh 31 tended to increase, and a distribution of the cell mass sizes tended to spread as a whole. When the flow rate was high, a distribution of the cell masses having a size close to the pore size of the mesh 31 tended to increase, and a distribution of the cell mass sizes tended to narrow as a whole.
[Opening Ratio of Mesh 31 of Subculturing Filter Portion 15]

For the mesh 31 of the subculturing filter portion 15, those having an opening ratio of 72% (formed with stainless steel, Pore size of 46 µm), 71% (formed with stainless steel, Pore size of 55 µm), 64% (formed with stainless steel, Pore size of 50 µm), and 58% (formed with PET, Pore size of 98 µm) were used, and the subculturing operation described above was performed about each mesh. The flow rate of the culture medium passing through the subculturing filter portion 15 was set to 90 mL per minute.

Figure 6:
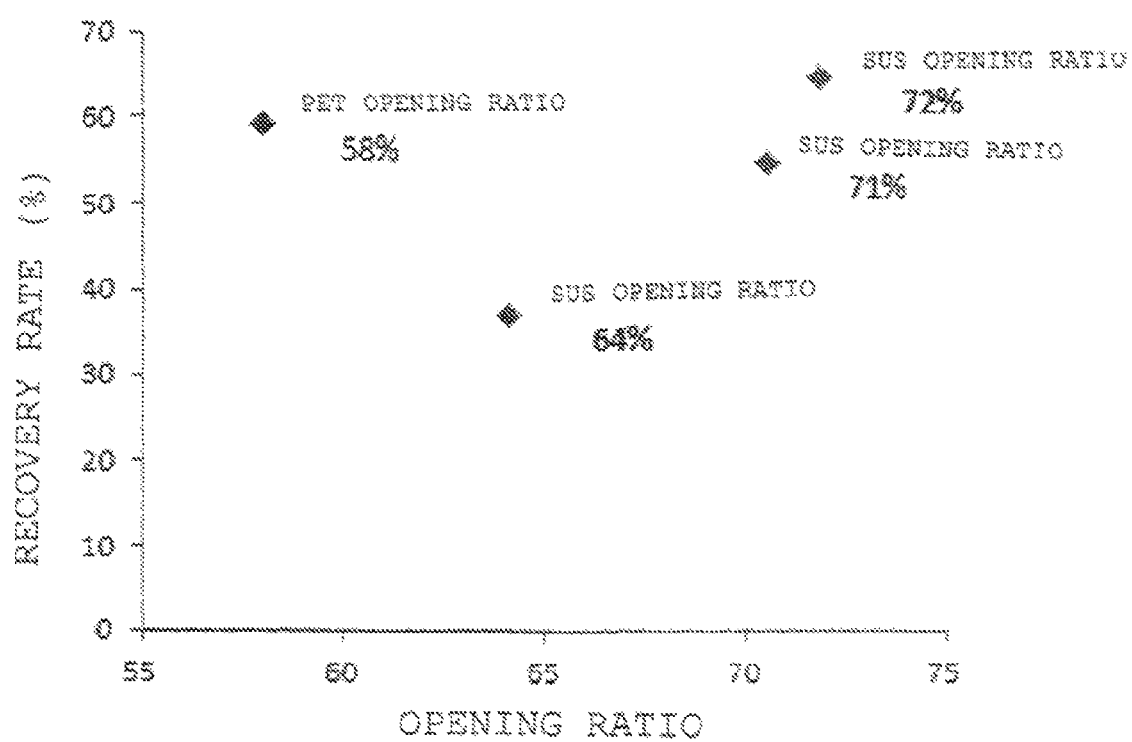
FIG. 6 shows the recovery rate of cells to the opening ratio of the mesh 31.

The results of determining the recovery rate for the mesh 31 of each opening ratio by calculation are shown in FIG. 6. As is clear from FIG. 6, the tendency was confirmed that, when the material of the mesh 31 was the same (formed with stainless steel), the recovery rate further improved when the opening ratio was higher.

REFERENCE SIGNS LIST

10 Culture system
11 Culture bag
12 Waste liquid container
13 Fresh culture medium container 14 Trap portion
15 Subculturing filter portion
16 Pump
17,18 Backwashing container
31 Mesh

The invention claimed is:

1. A culture system for pluripotent stem cells comprising:
a culture container for suspending and culturing pluripotent stem cells in a culture medium;
a waste liquid container which is connected to the culture container by flow channels through which liquid can flow and which stores a used culture medium flowing out of the culture container;
a fresh culture medium container which is connected to the culture container by flow channels through which liquid can flow and which stores a fresh culture medium to be supplied to the culture container;
first switching portions which switch the flow channels from the culture container to the waste liquid container or the fresh culture medium container;
a trap portion which is provided in the flow channel on a side of the culture container with respect to the first switching portions and which traps the pluripotent stem cells in the culture medium in flow to a side of the waste liquid container;
a subculturing filter portion which is provided in flow channels provided in parallel to a flow channel connecting the trap portion and the culture container between the trap portion and the culture container and which has a mesh capable of dividing a cell mass of the pluripotent stem cells; and
second switching portions which switch flow channels from the trap portion to the culture container or the subculturing filter portion.

2. The culture system for pluripotent stem cells according to claim 1, further comprising:
a backwashing container which is provided in a flow channel connecting the culture container and the subculturing filter portion in such a manner as to allow passage of liquid and which stores a backwashing culture medium to be supplied to the subculturing filter portion.

3. The culture system for pluripotent stem cells according to claim 1, further comprising:
a control portion for controlling a flow rate of liquid in each of the flow channels, wherein
the control portion sets a flow rate per unit square cm of liquid flowing through the mesh of the subculturing filter portion to 95 mL or more per minute.

4. The culture system for pluripotent stem cells according to claim 1, further comprising:
a pump for letting liquid flow through each of the flow channels; and
a control portion which controls drive of the pump, wherein
the control portion drives the pump at a fixed flow rate of 90 mL or more per minute at least in flow from the trap portion to the subculturing filter portion.

5. The culture system for pluripotent stem cells according to claim 1, wherein the pluripotent stem cells are ES cells or iPS cells.

6. The culture system for pluripotent stem cells according to claim 1, wherein the pluripotent stem cells are human-derived pluripotent stem cells.

7. A method for subculturing pluripotent stem cells comprising:
a culturing step of culturing suspending and culturing a cell mass of pluripotent stem cells;
a first dividing step of letting the cell mass of the cultured pluripotent stem cells flow into a mesh, which is provided in a flow channel through which a culture medium can flow, in one direction together with a culture medium to thereby divide the cell mass, and then accommodating the divided cell masses in a culture container;
a backwashing step of closing a flow channel to the culture container, and then letting the culture medium flow into the mesh in an opposite direction to the direction in the dividing process to remove a cell mass clogging the mesh; and
a second dividing step of opening the flow channel to the culture container, letting the removed cell mass flow in one direction together with the culture medium to thereby divide the cell mass, and then accommodating the divided cell masses in the culture container.

8. The method for subculturing pluripotent stem cells according to claim 7, wherein the pluripotent stem cells are ES cells or iPS cells.

9. The method for subculturing pluripotent stem cells according to claim 7, wherein the pluripotent stem cells are human-derived pluripotent stem cells.

* * * * *